(12) United States Patent
Choe

(10) Patent No.: US 9,439,847 B2
(45) Date of Patent: Sep. 13, 2016

(54) COMPOSITION FOR PREVENTING HAIR LOSS OR ENHANCING HAIR GROWTH COMPRISING CYCLOPHILIN A

(71) Applicant: UNIVERSITY-INDUSTRY COOPERATION GROUP OF KYUNG HEE UNIVERSITY, Yongin-si, Gyeonggi-do (KR)

(72) Inventor: Wonchae Choe, Seoul (KR)

(73) Assignee: UNIVERSITY-INDUSTRY COOPERATION GROUP OF KYUNG HEE UNIVERSITY, Yongin-Si (KR)

( * ) Notice: Subject to any disclaimer, the term of this patent is extended or adjusted under 35 U.S.C. 154(b) by 0 days.

(21) Appl. No.: 14/427,511

(22) PCT Filed: Sep. 10, 2013

(86) PCT No.: PCT/KR2013/008164
§ 371 (c)(1),
(2) Date: Mar. 11, 2015

(87) PCT Pub. No.: WO2014/042401
PCT Pub. Date: Mar. 20, 2014

(65) Prior Publication Data
US 2015/0209262 A1    Jul. 30, 2015

(30) Foreign Application Priority Data

Sep. 12, 2012 (KR) ........................ 10-2012-0101053

(51) Int. Cl.
| | |
|---|---|
| *A61P 17/14* | (2006.01) |
| *A61K 8/66* | (2006.01) |
| *A61K 48/00* | (2006.01) |
| *A61K 38/52* | (2006.01) |
| *A61K 8/60* | (2006.01) |
| *A61K 8/64* | (2006.01) |
| *A61Q 7/00* | (2006.01) |
| *A61Q 5/00* | (2006.01) |
| *G01N 33/573* | (2006.01) |
| *A61K 38/13* | (2006.01) |

(52) U.S. Cl.
CPC ............... *A61K 8/66* (2013.01); *A61K 8/606* (2013.01); *A61K 8/64* (2013.01); *A61K 38/52* (2013.01); *A61K 48/00* (2013.01); *A61Q 5/00* (2013.01); *A61Q 7/00* (2013.01); *C12Y 502/01008* (2013.01); *G01N 33/573* (2013.01); *A61K 2800/86* (2013.01); *G01N 2333/99* (2013.01); *G01N 2500/10* (2013.01)

(58) Field of Classification Search
None
See application file for complete search history.

(56) References Cited

U.S. PATENT DOCUMENTS

| | | |
|---|---|---|
| 2002/0165275 A1 | 11/2002 | Wu et al. |
| 2003/0055009 A1 | 3/2003 | Steiner et al. |
| 2005/0074438 A1 | 4/2005 | Kim et al. |
| 2010/0041747 A1 | 2/2010 | Fischer et al. |

FOREIGN PATENT DOCUMENTS

| | | |
|---|---|---|
| DE | 102009043486 A1 | 7/2010 |
| JP | 11-174041 A | 7/1999 |
| KR | 10-0641295 B1 | 10/2006 |
| WO | 2006084333 A1 | 8/2006 |
| WO | 2010054141 A2 | 5/2010 |

OTHER PUBLICATIONS

Li et al., Cancer 2006;106:2284-94.*
Beauchesne et al. 2007, Drug Development and Industrial Pharmacy, 33:211-220.*
Maurer et al., 1997, Am. J. Path. 150(4)1433-1441.*
Jerome Solassol et al., "FKBP family proteins as promising new biomarkers for cancer", Current Opinion in Pharmacology 2011, pp. 320-325, vol. 11, No. 4.
Sandra Ciesek et al., "Cyclosporine A Inhibits Hepatitis C Virus Nonstructural Protein 2 Through Cyclophilin A", Hepatology 2009, pp. 1638-1645, vol. 50, No. 5.
Nwe Nwe Soe, MD et al., "Cyclophilin A: A Mediator of Cardiovascular Pathology", Journal of the Korean Society of Hypertension, Dec. 2011, pp. 133-147, vol. 17, No. 4.
Grace Moscoso-Solorzano et al., "Cyclophilin A as a mediator of tissue injure and nephrotoxicity", Nephrology Reviews, Jul. 17, 2012, pp. 42-44, vol. 4, No. 2, Article No. e9.
International Searching Authority, International Search Report for PCT/KR2013/008164 dated Dec. 2, 2013.
European Patent Office, Communication dated Feb. 24, 2016, issued in corresponding European Application No. 13837042.4.

* cited by examiner

*Primary Examiner* — Doug Schultz
(74) *Attorney, Agent, or Firm* — Sughrue Mion, PLLC

(57) ABSTRACT

The present invention relates to a composition for preventing hair loss or enhancing hair growth which comprises a cyclophilin A (CypA) protein, a nucleic acid having a nucleotide sequence encoding the CypA protein, or a CypA protein expression recombinant vector. The composition of the present invention is administered into skin cells to inhibit the IL-1 expression of the skin cells, to modulate the activities of ERK and c-jun, and to increase the expression of NF-kB p65, thereby promoting the growth and development of hair follicles. Therefore, the composition of the present invention can be useful in preventing hair loss or enhancing hair growth.

2 Claims, 4 Drawing Sheets

SEQUENCE LISTING

<160> NUMBER OF SEQ ID NOS: 4

<210> SEQ ID NO 1
<211> LENGTH: 165
<212> TYPE: PRT
<213> ORGANISM: Homo sapiens

<400> SEQUENCE: 1

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu
                165

<210> SEQ ID NO 2
<211> LENGTH: 165
<212> TYPE: PRT
<213> ORGANISM: Artificial Sequence
<220> FEATURE:
<223> OTHER INFORMATION: Synthetic construct of PPIase activity defect
      mutant CypA R55A

<400> SEQUENCE: 2

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Ala Ile Ile Pro Gly Phe Met Cys Gln Gly
    50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

130                 135                 140
        Phe Gly Ser Arg Asn Gly Lys Thr Ser Lys Lys Ile Thr Ile Ala Asp
        145                 150                 155                 160

Cys Gly Gln Leu Glu
                        165

<210> SEQ ID NO 3
<211> LENGTH: 2276
<212> TYPE: DNA
<213> ORGANISM: Homo sapiens

<400> SEQUENCE: 3
gaacgtggta taaaagggc gggaggccag gctcgtgccg ttttgcagac gccaccgccg      60
aggaaaaccg tgtactatta gccatggtca accccaccgt gttcttcgac attgccgtcg     120
acggcgagcc cttgggccgc gtctcctttg agctgtttgc agacaaggtc ccaaagacag     180
cagaaaattt tcgtgctctg agcactggag agaaaggatt tggttataag ggttcctgct     240
ttcacagaat tattccaggg tttatgtgtc agggtggtga cttcacacgc cataatggca     300
ctggtggcaa gtccatctat ggggagaaat tgaagatga gaacttcatc ctaaagcata     360
cgggtcctgg catcttgtcc atggcaaatg ctggacccaa cacaaatggt tcccagtttt     420
tcatctgcac tgccaagact gagtggttgg atggcaagca tgtggtgttt ggcaaagtga     480
aagaaggcat gaatattgtg gaggccatgg agcgctttgg gtccaggaat ggcaagacca     540
gcaagaagat caccattgct gactgtggac aactcgaata agtttgactt gtgttttatc     600
ttaaccacca gatcattcct tctgtagctc aggagagcac ccctccaccc catttgctcg     660
cagtatccta gaatctttgt gctctcgctg cagttccctt tgggttccat gttttccttg     720
ttccctccca tgcctagctg gattgcagag ttaagtttat gattatgaaa taaaaactaa     780
ataacaattg tcctcgtttg agttaagagt gttgatgtag gctttatttt aagcagtaat     840
gggttacttc tgaaacatca cttgtttgct taattctaca cagtacttag attttttta     900 cttttccagtc ccaggaagtg tcaatgtttg ttgagtggaa tattgaaaat gtaggcagca     960
actgggcatg gtggctcact gtctgtaatg tattacctga ggcagaagac cacctgaggg    1020
taggagtcaa gatcagcctg gcaacatag tgagacgctg tctctacaaa aaataattag    1080
cctggcctgg tggtgcatgc ctagtcctag ctgatctgga ggctgacgtg ggaggattgc    1140
ttgagcctag agtgagctat tatcatgcca ctgtacagcc tgggtgttca cagatcttgt    1200
gtctcaaagg taggcagagg caggaaaagc aaggagccag aattaagagg ttgggtcagt    1260
ctgcagtgag ttcatgcatt tagaggtgtt cttcaagatg actaatgtca aaaattgaga    1320
catctgttgc ggtttttttt ttttttttt cccctggaat gcagtggcgt gatctcagct    1380
cactgcagcc tccgcctcct gggttcaagt gattctagtg cctcagcctc tgagtagct    1440 gggataatgg gcgtgtgcca ccatgcccag ctaatttttg tattttagt atagatgggg    1500 tttcatcatt ttgaccaggc tggtctcaaa ctcttgacct cagctgatgc gcctgccttg    1560
gcctcccaaa ctgctgagat tacagatgtg agccaccgca ccctacctca ttttctgtaa    1620
caaagctaag cttgaacact gttgatgttc ttgagggaag catattgggc tttaggctgt    1680
aggtcaagtt tatacatctt aattatggtg gaattcctat gtagagtcta aaaagccagg    1740
tacttggtgc tacagtcagt ctccctgcag agggttaagg cgcagactac ctgcagtgag    1800
gaggtactgc ttgtagcata tagagcctct ccctagcttt ggttatggag gctttgaggt    1860
tttgcaaacc tgaccaattt aagccataag atctggtcaa agggataccc ttcccactaa    1920

```
ggacttggtt tctcaggaaa ttatatgtac agtgcttgct ggcagttaga tgtcaggaca    1980
atctaagctg agaaacccc ttctctgccc accttaacag acctctaggg ttcttaaccc    2040
agcaatcaag tttgcctatc ctagaggtgg cggatttgat catttggtgt gttgggcaat    2100
ttttgtttta ctgtctggtt ccttctgcgt gaattaccac caccaccact tgtgcatctc    2160
agtcttgtgt gttgtctggt tacgtattcc ctgggtgata ccattcaatg tcttaatgta    2220
cttgtggctc agacctgagt gcaaggtgga aataaacatc aaacatcttt tcatta       2276
```

<210> SEQ ID NO 4
<211> LENGTH: 2276
<212> TYPE: DNA
<213> ORGANISM: Artificial Sequence
<220> FEATURE:
<223> OTHER INFORMATION: Synthetic construct of PPIase activity defect mutant CypA R55A

<400> SEQUENCE: 4

```
gaacgtggta taaaggggc gggaggccag gctcgtgccg ttttgcagac gccaccgccg    60
aggaaaaccg tgtactatta gccatggtca accccaccgt gttcttcgac attgccgtcg   120
acggcgagcc cttgggccgc gtctcctttg agctgtttgc agacaaggtc ccaaagacag   180
cagaaaattt tcgtgctctg agcactggag agaaaggatt tggttataag ggttcctgct   240
ttcacgcaat tattccaggg tttatgtgtc agggtggtga cttcacacgc cataatggca   300
ctggtggcaa gtccatctat ggggagaaat tgaagatga gaacttcatc ctaaagcata   360
cgggtcctgg catcttgtcc atggcaaatg ctggacccaa cacaaatggt tcccagtttt   420
tcatctgcac tgccaagact gagtggttgg atggcaagca tgtggtgttt ggcaaagtga   480
aagaaggcat gaatattgtg gaggccatgg agcgctttgg gtccaggaat ggcaagacca   540
gcaagaagat caccattgct gactgtggac aactcgaata agtttgactt gtgttttatc   600
ttaaccacca gatcattcct tctgtagctc aggagagcac ccctccaccc catttgctcg   660
cagtatccta gaatctttgt gctctcgctg cagttccctt tgggttccat gttttccttg   720
ttccctccca tgcctagctg gattgcagag ttaagtttat gattatgaaa taaaaactaa   780
ataacaattg tcctcgtttg agttaagagt gttgatgtag gctttatttt aagcagtaat   840
gggttacttc tgaaacatca cttgtttgct taattctaca cagtacttag atttttttta   900
ctttccagtc ccaggaagtg tcaatgtttg ttgagtggaa tattgaaaat gtaggcagca   960
actgggcatg gtggctcact gtctgtaatg tattacctga gcagaagac cacctgaggg   1020 taggagtcaa gatcagcctg gcaacatag tgagacgctg tctctacaaa aataattag    1080 cctggcctgg tggtgcatgc ctagtcctag ctgatctgga ggctgacgtg gaggattgc    1140 ttgagcctag agtgagctat tatcatgcca ctgtacagcc tgggtgttca cagatcttgt   1200
gtctcaaagg taggcagagg caggaaaagc aaggagccag aattaagagg ttgggtcagt   1260
ctgcagtgag ttcatgcatt tagaggtgtt cttcaagatg actaatgtca aaaattgaga   1320
catctgttgc ggtttttttt tttttttttt ccctggaat gcagtggcgt gatctcagct    1380
cactgcagcc tccgcctcct gggttcaagt gattctagtg cctcagcctc ctgagtagct   1440
gggataatgg gcgtgtgcca ccatgcccag ctaattttg tatttttagt atagatgggg   1500
tttcatcatt ttgaccaggc tggtctcaaa ctcttgacct cagctgatgc gcctgccttg   1560
gcctcccaaa ctgctgagat tacagatgtg agccaccgca ccctacctca tttttctgtaa   1620 caaagctaag cttgaacact gttgatgttc ttgagggaag catattgggc tttaggctgt   1680
```

-continued

```
aggtcaagtt tatacatctt aattatggtg gaattcctat gtagagtcta aaaagccagg    1740
tacttggtgc tacagtcagt ctccctgcag agggttaagg cgcagactac ctgcagtgag    1800
gaggtactgc ttgtagcata tagagcctct ccctagcttt ggttatggag gctttgaggt    1860
tttgcaaacc tgaccaattt aagccataag atctggtcaa agggataccc ttcccactaa    1920
ggacttggtt tctcaggaaa ttatatgtac agtgcttgct ggcagttaga tgtcaggaca    1980
atctaagctg agaaaacccc ttctctgccc accttaacag acctctaggg ttcttaaccc    2040
agcaatcaag tttgcctatc ctagaggtgg cggatttgat catttggtgt gttgggcaat    2100
tttgttttta ctgtctggtt ccttctgcgt gaattaccac caccaccact tgtgcatctc    2160
agtcttgtgt gttgtctggt tacgtattcc ctgggtgata ccattcaatg tcttaatgta    2220
cttgtggctc agacctgagt gcaaggtgga aataaacatc aaacatcttt tcatta        2276
```

COMPOSITION FOR PREVENTING HAIR LOSS OR ENHANCING HAIR GROWTH COMPRISING CYCLOPHILIN A

CROSS REFERENCE TO RELATED APPLICATIONS

This application is a National Sate of International Application No. PCT/KR2013/008164 filed Sep. 10, 2013, claiming priority based on Korean Patent Application No. 10-2012-0101053 filed Sep. 12, 2012, the contents of all of which are incorporated herein by reference in their entirety.

TECHNICAL FILED

The present invention relates to a composition for preventing hair loss or enhancing hair growth which comprises a cyclophilin A (CypA) protein, a nucleic acid having a nucleotide sequence encoding the CypA protein, or a CypA protein expression recombinant vector.

BACKGROUND ART

Hair is a body protection organ which is recognized as an additional integument structure together with sebaceous glands, sweat glands and nails. Hair growth is a circulation process that is very well controlled. In mammals, the hair growth is defined as three distinct phases of anagen (growing phase), catagen (regressing phase), and telogen (resting phase). During the period of catagen, the regression of hair follicles reflects a strictly controlled process characterized by a matrix remodeling such as a terminal differentiation and apoptosis of proximal epithelial hair bulb, perifollicular proteolysis, and follicular melanogenesis completion.

Hair loss is a disease that emotionally gives a pain to humans. Also, the hair loss is associated with many diseases of human. There are many causes of hais loss, including diseases, nutritional deficiency, aging, hormonal imbalance, and stress.

Growth and development of the hair follicles interact with numerous growth factors and cytokines. The most well-known factors include, for example, keratinocyte growth factor (KGF) and interleukin-1 (IL-1). In particular, the control of interleukin-1 is related directly to the growth and development of the hair follicles.

Annually estimated market for hair growth amounts to billions of dollars. However, only two drugs for preventing hair loss, i.e., minoxidil which is anti-hypertensive potassium channel opener, and finasteride which is dihydrotestosteron-suppressing 5a-reductase inhibitor, have been approved by the FDA. Among them, minoxidil has no clear report on the mechanism of action, and side effects such as mild scalp irritation and allergic dermatitis have been reported. Also, only about 30% of patients showed the effect of hair growth, and there are no effects other than ordinary patients with alopecia areata. Further, finasteride is known to have a mechanism of action which inhibits an enzyme activity acting on androgen metabolism. Side effects such as sexual debility, erectile dysfunction, and women breasts have been reported. In particular, due to the toxicity inherent to the drug, its use for pregnant women is prohibited.

In Korea, a number of researches associated with hair loss are currently in progress. In recent years, the hair growth effects of cyclosporine A, an immunosuppressive agent, have been reported. However, due to a number of side effects, for example, a liver toxicity, a hypertension, an immunosuppressive effect, a renal toxicity, an increase in neutral lipid, it is hard to actually apply to a clinical therapy.

Therefore, the development of a medicine for treating hair loss which has a low toxicity or side effect and an excellent effect is urgent.

On the other hand, Cyclophilins (Cyps) were first found as proteins having a high affinity to the immunosuppressive cyclosporin A (CsA). The cyclophilins acts on various cellular responses including a transcriptional regulation, an immune response, a protein secretion and a mitochondrial function control.

Cyclophilins have a peptidyl-prolyl cis-trans isomerase (PPIase) activity which catalyzes the cis-trans conversion of peptide bond into a proline residue at amino-terminal which facilitates a protein folding and an additional cellular process. In mammals, more than ten cyclophilin subtypes are included. Cyclophilin A is a protein spreaded everywhere belonging to the immunophilin family. Numerous researches on the function of cyclophilin A have been made in some diseases such as cancer cell resistance, Alzheimer's disease and hepatitis C virus replication. Further, cyclosporin A is known to act as a growth factor in vascular smooth muscle cells.

However, in diseases related to hair loss, the role of CypA associated with the prevention of hair loss and the enhancement of hair growth has not been found.

Under this background, the present inventors have found that cyclophilin A having a PPIase activity, one of the immunophilin family, can be used to prevent hair loss or enhance hair growth.

DISCLOSURE

Technical Problem

It is therefore an object of the present invention to provide a composition for preventing hair loss or enhancing hair growth which comprises a cyclophilin A (CypA) protein.

It is another object of the present invention to provide a composition for preventing hair loss or enhancing hair growth which comprises a nucleic acid having a nucleotide sequence encoding the CypA protein.

It is still another object of the present invention to provide a composition for preventing hair loss or enhancing hair growth which comprises a CypA protein expression recombinant vector.

It is a further object of the present invention to provide a method for screening a drug for preventing hair loss or enhancing hair growth by identifying a substance that promotes the expression of the CypA protein.

Technical Solution

According to one aspect of the present invention, a composition for preventing hair loss or enhancing hair growth which comprises a cyclophilin A (CypA) protein is provided.

The CypA protein used in the composition of the present invention includes all CypA proteins derived from yeast, plant or animal. The CypA protein includes a wild type and also a variant of the CypA protein by deletion, insertion, non-conservative or conservative substitution or a combination thereof if it functions to prevent hair loss or enhance hair growth. Specific examples may include a wild type CypA protein having the amino acid sequence of SEQ ID NO: 1, or a CypA protein having the amino acid sequence of SEQ ID NO: 2 with a defect in the activity of PPIase enzyme. The variants with substitution, insertion or deletion of such sequences may be used in the composition of the present invention.

The variant of the CypA protein refers to a protein wherein one or more amino acid residues have a different sequence(s) as compared with a wild-type amino acid sequence. The insertion is typically made of a continuous sequence of about 1 to 20 amino acids, but a larger insertion can be made. The deletion is typically made of about 1 to 30 residues, but in some cases a greater deletion can be made as one of the domains may be deleted. The variants may be prepared by a chemical peptide synthesis method known in the art or by a recombinant method based on DNA sequence (see Sambrook et al., Molecular Cloning, Cold Spring Harbour Laboratory Press, New York, USA, 2d Ed., 1989). Amino acid exchanges in proteins and peptides that do not wholly change the activities of the molecules are known in the art (see H. Neurath, R L Hill, The Proteins, Academic Press, New York, 1979). The most commonly occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly.

Further, the CypA protein may be modified with phosphorylation, sulfation, acrylation, glycosylation, methylation, farnesylation and the like, as desired.

The variants or modifiers are functional equivalents which show the same biological activities as the natural protein, but in some cases, they may be variants or modifiers which have changed the properties of the protein. Proteins with increased structural stability against heat, pH, etc. or increased activities by the mutation or modification of the amino acid sequences are preferred.

The CypA protein can be obtained by extraction and purification from nature by means of methods well known to those skilled in the art. Alternatively, because the sequences of the CypA protein have been identified, it may be chemically synthesized (see Merrifleld, J. Amer Chem Soc, 85:2149-2156, 1963), or obtained by using a gene recombination technique. When prepared by the chemical synthesis, polypeptide synthesis methods well known in the art can be used. When using a gene recombinant technique, the CypA protein can be obtained by inserting a nucleic acid encoding the CypA into an appropriate expression vector, transforming the vector into a host cell, culturing the host cell so that the CypA is expressed, and then recovering the CypA from the host cell.

As the expression vector for expressing the CypA protein, all conventional expression vectors may be used. The expression level and modification of the protein differ depending on the host cell, so it is necessary to select the host cell most suitable for the purpose. The host cell which may be used includes lower eukaryotic cells such as fungus (e.g., *Aspergillus*), yeast (e.g., *Pichia pastoris*), *Saccharomyces cerevisiae, Schizosaccharomyces*, and *Neurospora crassa*, insect cells, plant cells, and cells derived from higher eukaryote including mammals.

After the protein is expressed in a selected host cell, conventional biochemical separation techniques, for example, treatment with a protein precipitating agent (salting out), centrifugation, ultrasonic disruption, ultrafiltration, dialysis, molecular sieve chromatography (gel filtration), adsorption chromatography, ion exchange chromatography, affinity chromatography and the like can be used for the isolation and purification thereof. Typically, in order to separate the protein with a higher purity, they can be used in combination (see Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif. (1990)).

According to another aspect of the invention, a composition for preventing hair loss or enhancing hair growth which comprises a nucleic acid having a nucleotide sequence encoding the cyclophilin A (CypA) protein is provided.

In the composition of this invention, the nucleotide sequence encoding the CypA protein is a nucleotide sequence encoding a wild-type or mutant form of the CypA protein as described above, wherein one or more bases may be mutated by substitution, deletion, insertion, or a combination thereof. Further, it may be isolated from nature or prepared using a chemical synthesis method.

When the nucleotide sequence encoding the CypA protein is chemically synthesized, synthesis methods well known in the art, for example, the method described in Engels and Uhlmann, Angew Chem IntEd Engl, 37. 73-127, 1988 may be used. The triester, phosphite, phosphoramidite and H-phosphate methods, PCR and other auto primer methods, oligonucleotide synthesis methods on solid support can be used.

Specific examples of the nucleotide sequence encoding the CypA protein may include a nucleotide sequence encoding the amino acid sequence of SEQ ID NO: 1 or SEQ ID NO: 2, a nucleotide sequence of SEQ ID NO: 3 as a sequence encoding an amino acid sequence of SEQ ID NO: 1; or a nucleotide sequence of SEQ ID NO: 4 as a sequence encoding an amino acid sequence of SEQ ID NO: 2.

The nucleic acid having the nucleotide sequence may be a single chain or a double chain, and a DNA molecule (genome, cDNA or synthesis) or a RNA molecule.

In a preferred embodiment, the nucleotide sequence encoding the CypA protein is provided on a recombinant expression vector operably linked to a vector expressing it.

In the present invention, the term "vector" refers to a means for introducing a nucleic acid sequence encoding a desired gene (e.g., DNA, RNA, etc.) into a host cell. In the present invention, the term "expression vector" refers to a vector capable of expressing a desired protein or a desired RNA in a suitable host cell, and to a gene construct including an essential regulatory element operably linked so that the gene insert is expressed.

In the present invention, the term "operably linked" refer to a state wherein a nucleic acid expression regulatory sequence is functionally linked to a nucleic acid sequence encoding a desired protein or RNA so as to perform a general function. For example, a promoter and a nucleic acid sequence encoding a protein or RNA may be operably linked to affect the expression of the coding sequence. The operable linkage to a recombinant vector may be prepared using a gene recombinant technique well known in the art. Site-specific DNA cleavage and linkage may use an enzyme commonly known in the art.

The vector of the present invention includes plasmid vector, cosmid vector, virus vector and the like. Suitable expression vectors include an expression regulatory element such as a promoter, an operator, an initiation codon, a termination codon, a polyadenylated signal, and an enhancer, a signal sequence or a leader sequence for membrane targeting or secretion, and may be variously prepared depending on the purposes. The initiation codon and termination codon are generally considered to be a part of a nucleotide sequence encoding a target protein. They must necessarily act on a subject when the gene construct is administered, and they must exist in the coding sequence in frame. The promoter of the vector may be constructive or inducible. The expression vector also includes a selectable marker for selecting host cells containing the vector. In the case of a replicable expression vector, it includes a replication origin. The vector may be self-replicable or integrated into a host DNA.

The nucleic acid having the nucleotide sequence encoding the CypA protein is directly injected by a method known in the art, for example, in a vector form of naked DNA (see Wolff et al, Science, 247:1465-8, 1990; Wolff et al., J Cell Sci 103: 1249-59, 1992), or delivered using liposome, cationic polymer, etc. into the cells of a patient for the purpose of treatment or prevention of hair loss disorders. Liposome is a phospholipid membrane prepared by mixing cationic phospholipids such as DOTMA and DOTAP for gene delivery. If cationic liposome is mixed with an anionic nucleic acid in a certain ratio, a nucleic acid-liposome complex is formed. This complex performs endocytosis in the cell to stay in the endosome (see Schaefer-Ridder M et al, Science, 215 (4529):166-168, 1982; Hodgson et al, Nat Biotechnol, 14 (3):339-342, 1996).

The degree of moving the gene flowed into the endosome to the nucleus via the cytoplasm determines the gene transfer and therapy efficiency. Such gene transfer method has a low immunogenicity and so repeated administration is available. Further, the method has a high safety.

The cationic polymer used in the gene transport include poly-L-lysine, spermine, polyethyleneimine (PEI), chitosan and the like (see Hashida, Br J Cancer., 90 (6):1252-1258, 2004; Wiseman, Gene Ther, 10 (19):1654-1662, 2003; Koping-Hoggard, Gene Ther, 8 (14):1108-1121, 2001). When a gene is administered in vivo in the form of a complex with a cationic polymer, the in-vivo residence time and the duration of expression of the gene were found to increase significantly as compared to a naked DNA.

In another aspect, the invention provides a composition for preventing hair loss or enhancing hair growth which comprises a CypA protein expression recombinant vector. The CypA protein expression recombinant vector may comprise a nucleotide sequence encoding the amino acid sequence of SEQ ID NO: 1 or SEQ ID NO: 2. It may also comprise the nucleotide sequence of SEQ ID NO: 3 or SEQ ID NO: 4.

If the recombinant vector engineered to express the CypA is transfected into the cells of a patient with hair loss, the therapeutic effect is excellent since the expression efficiency can be increased.

The vector used in the gene therapy may be viral vector. It includes, for example, but not limited to, replication defective retrovirus, adenovirus and adeno-associated virus. The viral vector has to meet the following criteria:

(1) The vector should be able to infect desired cells. The viral vector having an appropriate host range has to be selected accordingly;

(2) The delivered gene must be able to be expressed and preserved in the cells for an appropriate period; and (3) The vector should be safe to the host.

The other viral vectors that can be used for the gene delivery into the cells include retrovirus such as Moloney Murine Leukemia virus (M-MLV); parvovirus such as JC, SV40, polyoma, and adenovirus; Epstein-Barr virus (EBV); papillomavirus such as bovine papillomavirus type I (BPV); Vaccinia, poliovirus and other human and animal viruses. Alternatively, many methods and delivery vehicles including non-viral and non-proteinaceous vector, liposome-encapsulated DNA, lipid delivery vehicle, and naked DNA can be used.

Host expression systems are well known in the field to which the present invention pertains, and used in various aspects. A mammalian promoter may be any DNA sequences which can be combined with a mammalian RNA polymerase, and initiate downstream (3') transcription of the coding sequence of the cyclophilin protein to mRNA.

A promoter typically has a transcription initiation site positioned close to the 5' end of a coding sequence, and a TATA box using 25 to 30 base pairs positioned in upstream of the transcription initiation site. The TATA box is believed to direct RNA polymerase II so that RNA synthesis can be done at a correct position. The mammalian promoter also typically contains an upstream promoter element which is positioned in upstream of 100 to 200 base pairs of the TATA box. The upstream promoter element determines transcription initiation rate, and can function in either direction. The promoter that can be particularly used as the mammal promoter is derived from a mammalian virus gene. This is because the viral gene often is highly expressed and has a broad host range. Examples thereof may include SV40 early promoter, mouse mammary tumor virus LTR promoter, adenovirus major late promoter, and herpes simplex virus promoter.

As one example, this can be accomplished by operably linking the cyclophilin gene to a promoter which is very tightly controlled, like T7 expression vector (see Rosenberg, et al, Gene, 56: 125-135, 1987). Insertion into a potent vector may be achieved by identifying a convenient limited target near the both ends of the cyclophilin gene and a suitable limited target for vector near the promoter, and inserting the cyclophilin gene to the vector so that the cyclophilin gene can be oriented under the control of the transcription and translation of the potent promoter. Alternatively, the cyclophilin gene can be over-expressed by setting a potent ribosome binding site in upstream of the gene to increase the expression of the gene (see Shine and Dalgarno, Proc Natl Acad Sci USA, 71:1342-1346 1974).

Typically, the transcription termination and polyadenylated sequence recognized by the mammal cells are regulatory sites at the position 3' of the translation termination codon and thus adjacent to the coding sequence together with a promoter element. The 3' end of mature mRNA is formed by cleavage and polyadenylation after site-specific translation. The transcription terminator and polyadenylation signal include, for example, those derived from SV40.

The composition of the present invention comprising a cyclophilin A (CypA) protein, a nucleic acid having a nucleotide sequence encoding the CypA protein, or a CypA protein expression recombinant vector as described above can be used in preventing or treating hair loss disorders.

The composition of the present invention may be formulated in the form of injection or applying agent by a conventional method in combination with carriers that are commonly accepted in the pharmaceutical field. The injectable composition is preferably isotonic aqueous solutions or suspensions. The above-mentioned composition is sterilized and/or contains auxiliaries, for example, preservatives, stabilizers, wetting agents, emulsifying solution promoters, salts for adjusting osmotic pressure or buffering agents. In addition, it may also contain other therapeutically valuable substances.

The pharmaceutical preparation obtained thus can be administered by a parenteral manner as desired, that is, by subcutaneous or topical application. The dosage can be 0.001 μg ~10 mg/kg per day and be administered once or over several times. The dose level for any particular patient can vary depending on the patient's weight, age, gender, health condition, administration time, administration method, and severity of disease.

In addition, the applying agent according to the present invention can be easily produced in any form by a conventional method. In the preparation of a cream-type applying agent as one example, the CypA protein, etc. of the present invention is added to a typical oil-in-water type (O/W) or water-in-oil type (W/O) cream base, and a flavoring agent, a chelating agent, a pigment, an antioxidant and an antiseptic are added as required. For the purpose of improving physical properties, the applying agent can further comprise synthetic or natural materials such as protein, mineral, and vitamin.

According to another aspect, the present invention provides a method for screening a drug for preventing hair loss or enhancing hair growth, which comprises (a) culturing cyclophilin A (CypA) protein expression cells; (b) contacting the cells of step (a) with a candidate compound; (c) comparing an expression level of the cyclophilin A (CypA) protein in step (b) with an expression level of a control group not contacted with the candidate compound; and (d) identifying a drug showing an increase in the expression level of the cyclophilin A (CypA) protein. In the above method, the difference in the expression levels of the CypA protein can be found with the protein level or mRNA level. Using the screened drug, the CypA expression level in the cells may be increased; preferably, the CypA expression level in the skin cells can be increased.

The protein expression level can be confirmed through electrophoresis after each protein is loaded on a gel. Preferably, it can be confirmed by immunoassay through the amount of formation of an antigen-antibody complex using an antibody for the CypA protein. These analysis methods include a Western blot, RIA, immunoprecipitation assay and the like.

In the above method for detection, the amount of formation of the antigen-antibody complex can be quantitatively measured by the magnitude of a signal of a detection label. Such detection label can be selected from the group consisting of, but are not limited to, enzymes, fluoresceins, ligands, luminescent substances, microparticles, redox molecules and radioactive isotopes. The formation of the antigen-antibody complex can be detected using the method selected from the group consisting of, but not limited to, a colorimetric method, an electrochemical method, a fluorimetric method, a luminometry, a particle counting method, a visual assessment and a scintillation counting method.

The mRNA expression level can be confirmed by using a primer specific to the CypA protein. Specific analysis methods include RT-PCR, Northern blot and the like. It is preferable to use RT-PCR, a convenient analysis method capable of quantitatively measuring the transfer of CypA to mRNA by confirming the pattern and intensity of bands.

In the examples of the present invention, it has been specifically confirmed that the treatment of the CypA protein inhibits the expression of IL-1, modulate the activities of ERK and c-jun, and increase the expression of NF-kB p65, thereby promoting the growth and development of hair follicles, and preventing hair loss and enhancing hair growth.

Advantageous Effects

The composition comprising a cyclophilin A protein according to the present invention is administered in skin cells to inhibit the IL-1 expression of the skin cells, to modulate the activities of ERK and c-jun, and to increase the expression of NF-kB p65, thereby promoting the growth and development of hair follicles. Therefore, the composition of the present invention can be useful in preventing hair loss or enhancing hair growth.

BSET MODE

Figure 1A:
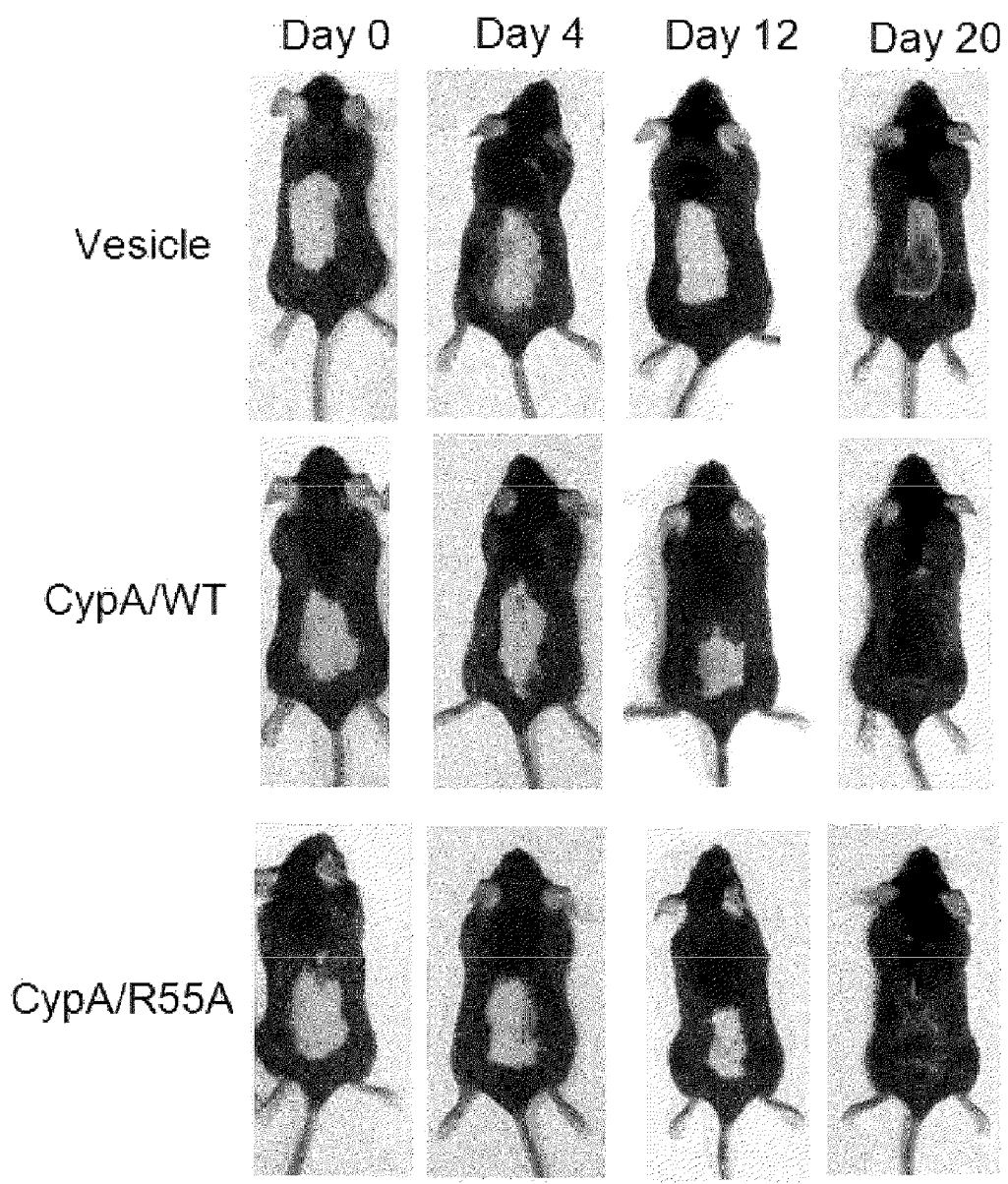
FIGS. 1a and 1b are a photograph and graph showing the effects that the CypA/WT protein has on the hair growth of C57BL/6 mice.

The present invention is further illustrated by the following examples, which are not to be construed to limit the scope of the invention.

Materials and Methods

EXAMPLE 1

Preparation of Recombinant Protein

The nucleotides of SEQ ID NO: 3 and SEQ ID NO: 4 were inserted into pGEX-KG vectors, respectively, preparing recombinant vectors, which were transformed into Top10F bacterial cells. 5 ml of the transformed bacteria were inoculated into a LB medium containing 100μg/ml of ampicillin (Luria broth, 500 ml), and then cultured overnight at 37° C. using an orbital shaker. The bacteria were cultured until the A600 (Absorption 600) became 0.4, inducted using 0.2 mM of isopropyl-1-thio-b-D-galactopyranoside (Sigma Aldrich, Germany), and then stirred at 37° C for 4 hours. The culture medium was centrifuged at 3000 rpm for 30 minutes to obtain cells. The pellet was then suspended in a PBS-T solution containing 200 mM PMSF. The suspended bacterial cells were lysed using sonication (20 second pulse interval 15 minutes, repeating 5 times). The recombinant proteins were purified by binding to glutathione-Sepharose (Sigma Aldrich, Germany), cut with thrombin (Sigma Aldrich, Germany) and then eluted with phosphate-buffered saline to obtain GST-hCypA/WT and GST-hCypA/R55A recombinant proteins.

EXAMPLE 2

Experimental Animals

Female C57BL/6 mice 6 week-aged after birth were purchased from the Central Laboratory Animal (Seoul, Korea). Food and water were supplied to the mice for one week to acclimate to the environment of the animal breeding facility. Four mice were used as one group. Three groups, that is, a total of 12 mice, were used in this experiment. The backs of the mice 7 week-aged after birth, of which all hair follicles enter into a telogen stage, were shaved carefully with scissors. From the next day after shaving (Day 1), each group was treated with 10 μg CypA/R55A recombinant protein, 10 μg (approximately 60 μM) CypA/WT recombinant protein, or 10 μl elution buffer (Comparative Example, vesicle) every day. At the time of passage of day 1, day 4, day 12, and day 20, one mouse was sacrificed from each experimental group to obtain a skin specimen.

EXAMPLE 3

Immunoblot Analysis

The mouse skin tissue was homogenized with an elution buffer (50 mM Tris-Cl, 150 mM NaCl, 5 mM EDTA, 0.1% NP-40) containing sodium vanadate ($NaVO_2$) and protease inhibitor cocktail (Jean-de-Port, South Korea). The whole lysate was loaded on a SDS-PAGE gel (12%), subjected to electrophoresis, and then transferred to a nitrocellulose membrane.

The above membrane was blocked with 5% BSA for one hour, washed, and then cultured overnight at 4° C. with a primary antibody. Then, it was culture for 45 minutes with a secondary antibody. The proteins were visualized with an enhanced Western Blotting Luminol reagent (Santa cruz Biotechnology; Santa Cruz, Calif., USA).

EXAMPLE 4

Histological Study

The dorsal skin was kept in 4% paraformaldehyde, embedded in an optimal cutting temperature (OCT) compound machine (Leica Microsystems, USA), and then rapidly frozen. 12 μm of section was mounted on a gelatin-coated slide. The section was stained with hematoxylin and eosin.

EXAMPLE 5

Immunohistochemistry

The level of expression of each protein was analyzed by immunohistochemistry. The sample was fixed with methanol (MeOH) for 5 minutes at 4° C., and then blocked with 2% normal goat serum (Vector laboratories, USA) for two hours at a room temperature. The blocked specimen was cultured overnight at 4° C. with a monoclonal primary antibody, washed with a PBS solution, and then allowed to react with a peroxidase-coupled secondary antibody. The immunostained section was visualized using a Dako EnVision Detection Kit (Dako, Denmark).

Results

1. CypA Protein-Induced Hair Growth in Mice

In order to study the function of the CypA protein in hair growth, the CypA protein was topically applied on the dorsal skin of the C57BL/6 mouse every day, and the change in skin color was observed. If black pigmentation occurs, it may verify that hair follicles have been transferred from a telogen phase to an anagen phase. The color of the dorsal skin was changed from 12 days after the topical treatment. After 20 days of the treatment, the last observed day, the mouse skin treated with CypA/WT protein showed much longer and thicker hair growth (FIG. 1a).

Figure 1B:
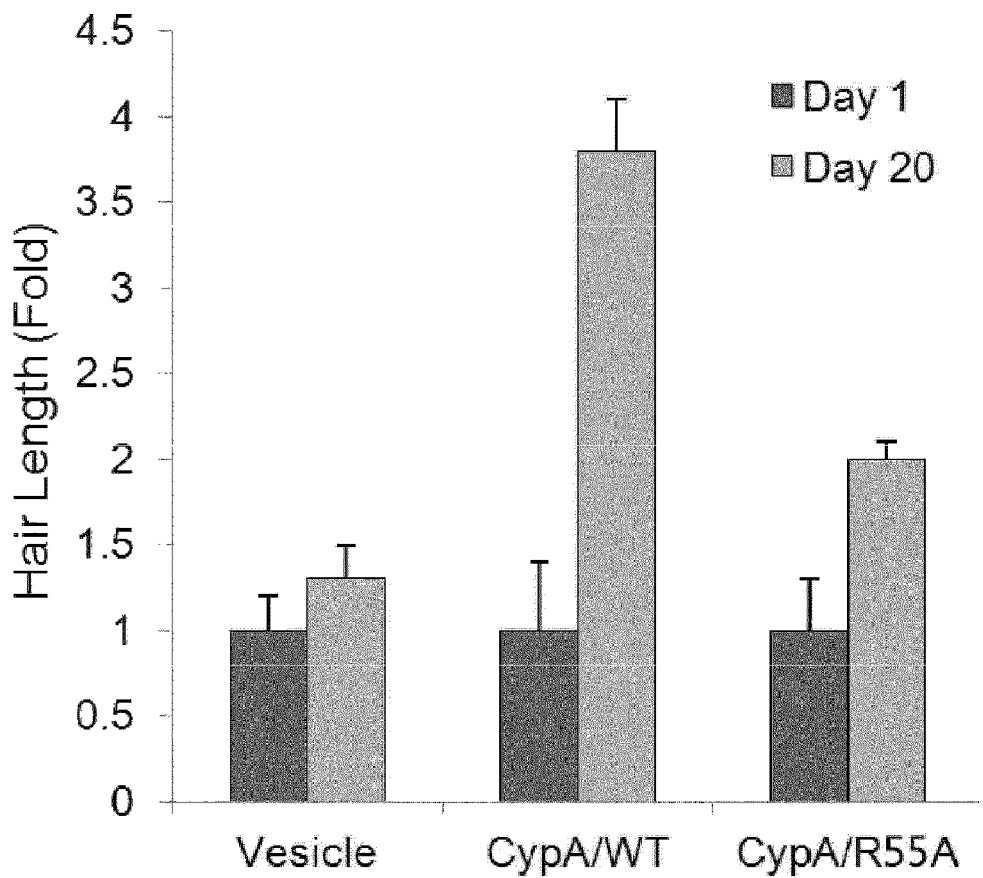

The average lengths of five hairs (n=5) randomly picked after one day and 20 days of the topical treatment were measured. Compared to the mouse of the comparative example, CypA/WT protein treatment showed approximately 3.5 times promotion of hair growth. The treatment with the mutant CypA/R55A protein lacking PPIase (peptidyl-prolyl isomerases) enzyme activity also showed similar effects to the results of the CypA/WT protein treatment (FIG. 1b).

2. Effects of CypA Protein Having on Hair Follicle Number and Elongation

Figure 2:
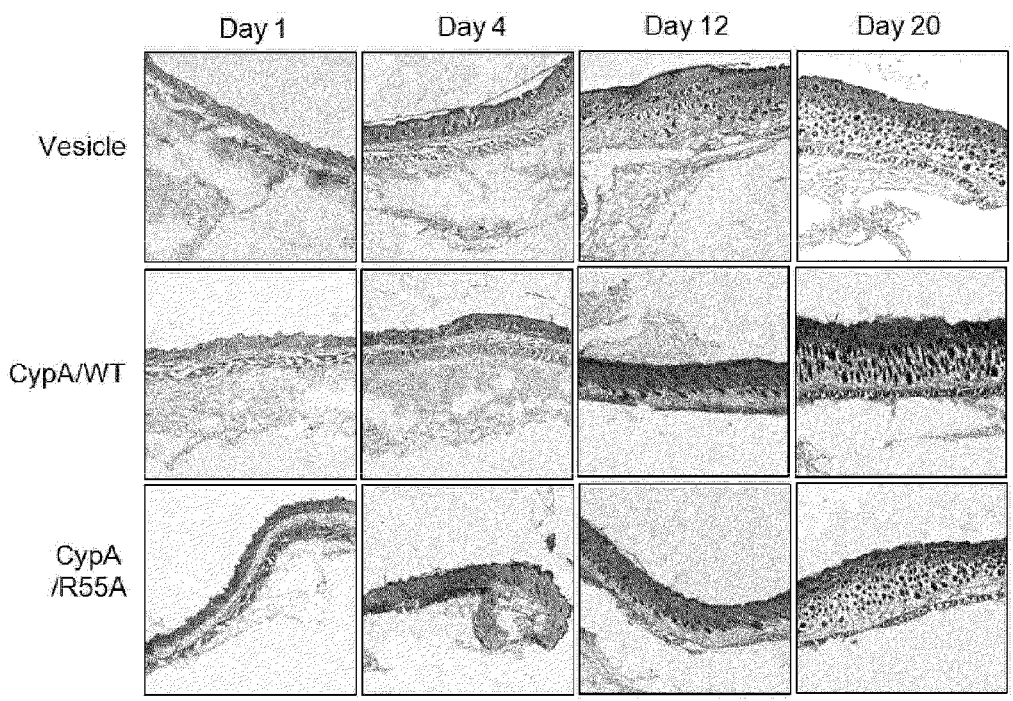
FIG. 2 is a photograph showing the histological features of mouse skin of a comparative example (Vesicle), CypA/WT protein treatment group, and CypA/R55A protein treatment group.

In order to investigate the role of the CypA protein acting on the growth of hair follicles, the dorsal skin sample of the mouse was stained with hematoxylin and eosin. Compared with the Comparative Example (vesicle), it was observed that the mouse treated with the CypA/WT mouse protein had more elongated hair follicles from 12 days (FIG. 2).

3. Identification of Proteins that are Variously Controlled by CypA Protein

Figure 3A:
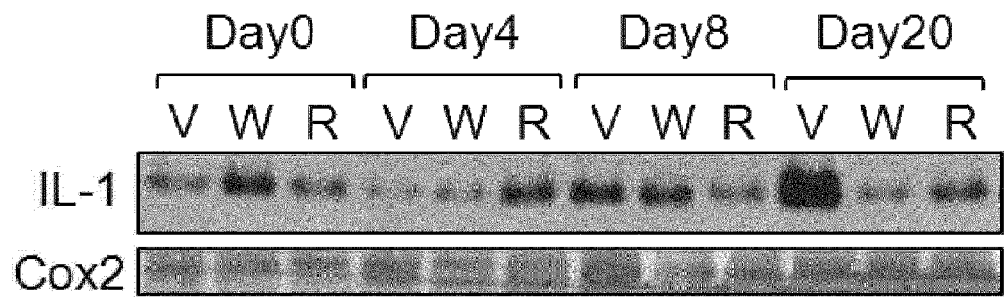
FIGS. 3a to 3c are diagrams showing the expression levels of proteins in C57BL/6 mouse skin after treatment with Vesicle (V), CypA/WT protein (W), and CypA/R55A protein (R).

The expression of various proteins was analyzed in order to determine the hair growth control of the CypA protein. Each sample was homogenized, separated by SDS-PAGE, and then detected with antibodies. First, the expression of interleukin-1 (IL-1) and cyclooxygenase 2 (Cox 2) was monitored. Inflammation and related physiological phenomena are one of the causes of hair loss. Interleukin-1 alpha (IL-1α) and Interleukin-1 beta (IL-1β) are cytokines involved in the control of immune response, inflammatory response, and hematopoiesis. In addition, IL-1 is well known to cause the inhibition of hair growth. Further, Cox 2 is closely related to the control of inflammation and pain. The pharmacological inhibition of the COX expression may provide for relief of inflammation and pain. As shown in FIG. 3a, the treatment with the CypA/WT protein inhibited the expression of IL-1. However, the expression of Cox 2 had no difference between the comparative example (vesicle) and CypA/WT treated sample.

Figure 3B:
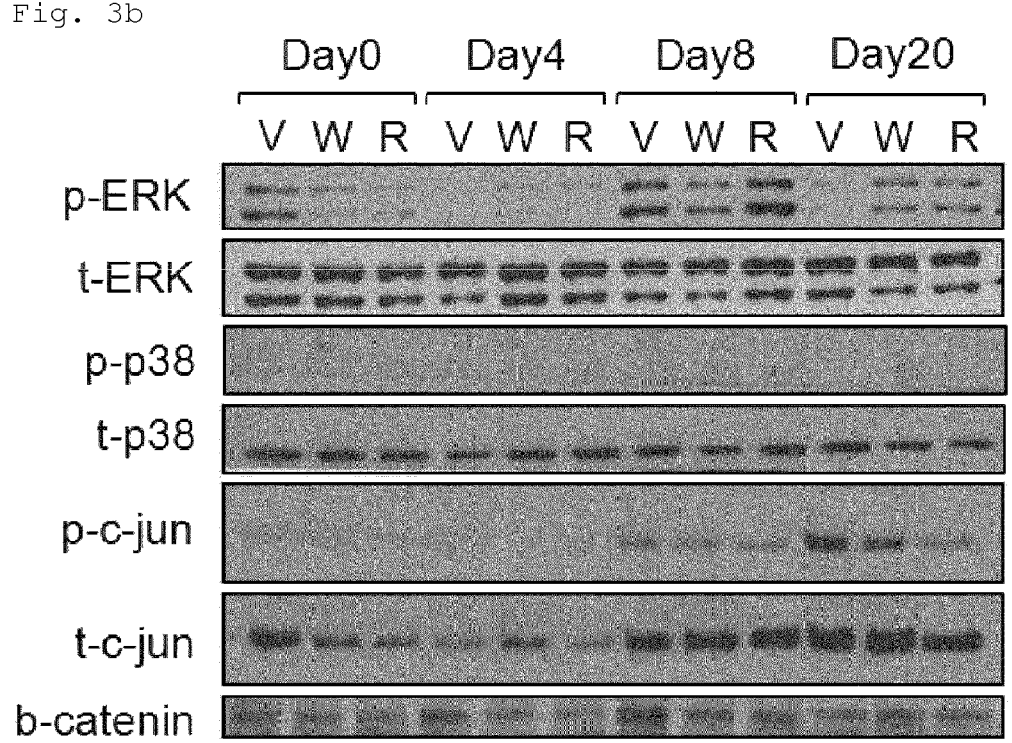

Next, the expression of kinase associated with cell proliferation such as ERK, p38 and c-jun was monitored. As shown in FIG. 3b, the CypA/WT protein modulated the activities of ERK and c-jun, but did not show any significant difference in the activity of p38.

Figure 3C:
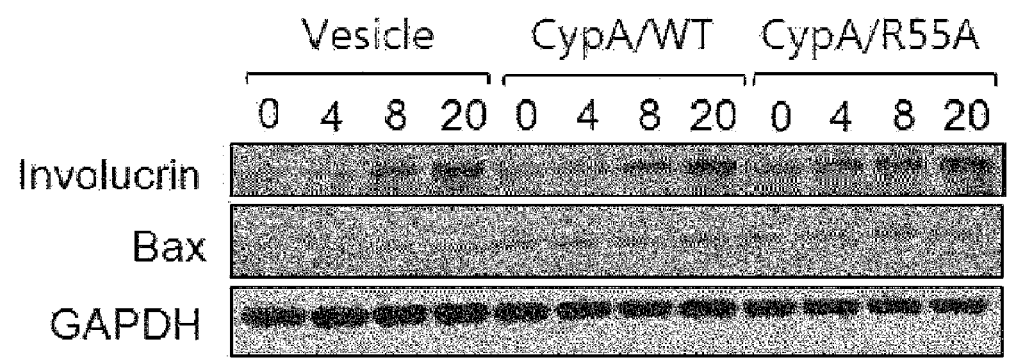

Finally, the expression levels of involucrin, a terminal differentiation marker, and bax, a proapoptosis marker, were measured. As a result, the treatment with the CypA/WT protein did not affect the expression of the differentiation and proapoptosis markers (FIG. 3c).

4. Regulation of NF-kB p65 Expression by CypA/WT Protein

The level of expression of NF-kB p65 in the skin sample was analyzed. NF-kB p65 is one of the target materials for the growth and development of hair follicles. Activated NF-kB controls downstream genes such as Wnt and Shh. As a result, the hair follicles are induced to be grown or developed.

Figure 4:
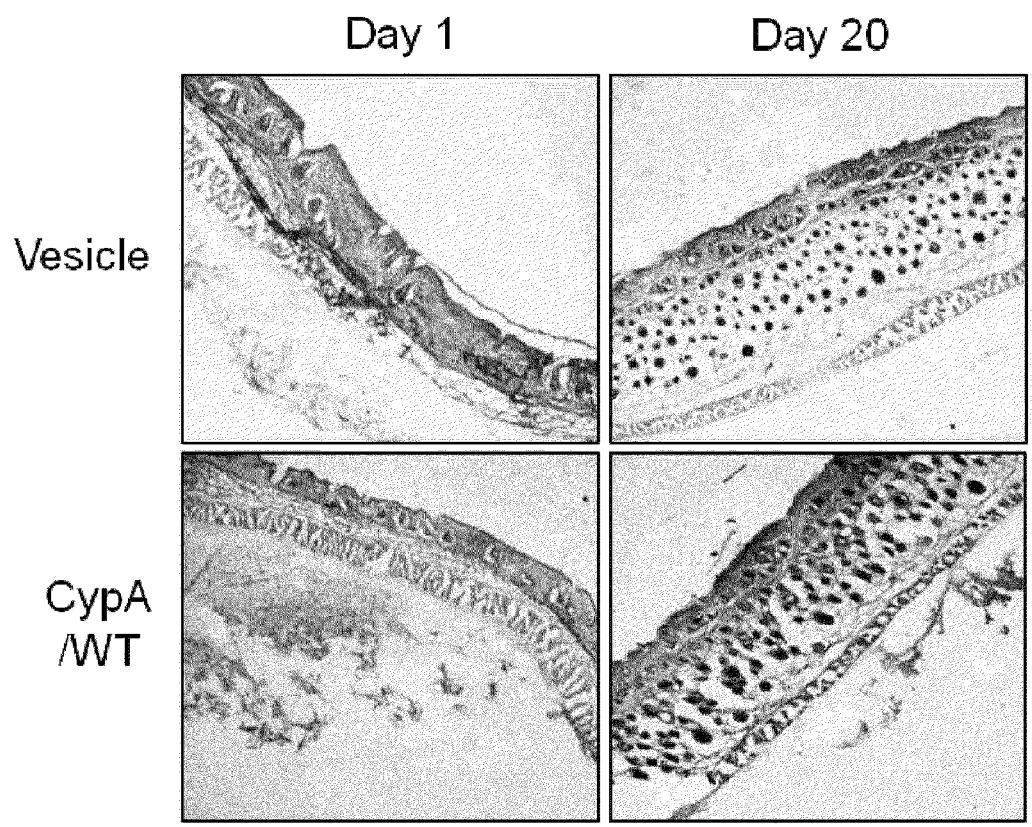
FIG. 4 is a view showing the inducible expression of NF-kB p65 after topical treatment with a comparative example (Vesicle) and the CypA/WT protein in C57BL/6 mouse skin.

As the analysis result, the expression of NF-kB p65 in the mouse skin treated with CypA/WT was increased (FIG. 4).

The invention claimed is:

1. A method for preventing hair loss or enhancing hair growth which comprises topically or subcutaneously administering a cyclophilin A (CypA) protein to a subject in need thereof.

2. The method of claim 1, wherein the CypA protein has the amino acid sequence of SEQ ID NO: 1 or SEQ ID NO: 2.

* * * * *